US010646261B2

(12) United States Patent
Folger et al.

(10) Patent No.: US 10,646,261 B2
(45) Date of Patent: May 12, 2020

(54) MULTI-PURPOSE SCREWDRIVER AND METHOD OF USE

(71) Applicant: Warsaw Orthopedic, Inc., Warsaw, IN (US)

(72) Inventors: Leigh Anna Folger, Marion, AR (US); Rex W. Armstrong, Cordova, TN (US); David A. Mire, Collierville, TN (US); Russell P. Nockels, Chicago, IL (US); Ian J. Harding, Bristol (GB)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/043,372

(22) Filed: Jul. 24, 2018

(65) Prior Publication Data

US 2020/0030009 A1    Jan. 30, 2020

(51) Int. Cl.
*A61B 17/70* (2006.01)
*A61B 17/88* (2006.01)

(52) U.S. Cl.
CPC ...... *A61B 17/7082* (2013.01); *A61B 17/7091* (2013.01); *A61B 17/8886* (2013.01)

(58) Field of Classification Search
CPC .. A61B 17/7074–7082; A61B 17/8875; B25B 15/00–06
USPC .......................... 81/436–461, 476; 606/86 A
See application file for complete search history.

(56) References Cited

U.S. PATENT DOCUMENTS

| 1,920,821 | A |   | 8/1933 | Wassenaar |
|---|---|---|---|---|
| 4,957,495 | A |   | 9/1990 | Kluger |
| 5,129,899 | A |   | 7/1992 | Small et al. |
| 5,219,349 | A |   | 6/1993 | Krag et al. |
| 5,458,030 | A | * | 10/1995 | Betts ............ B25B 23/005 81/451 |
| 5,885,286 | A |   | 3/1999 | Sherman et al. |
| 6,565,566 | B1 |   | 5/2003 | Wagner et al. |
| 6,648,891 | B2 |   | 11/2003 | Kim |
| 6,669,697 | B1 |   | 12/2003 | Pisharodi |
| 6,921,400 | B2 |   | 7/2005 | Sohngen |
| 6,932,819 | B2 |   | 8/2005 | Wahl et al. |
| 7,207,992 | B2 |   | 4/2007 | Ritland |
| 7,416,553 | B2 |   | 8/2008 | Patel et al. |
| 7,578,822 | B2 |   | 8/2009 | Rezach et al. |
| 7,618,424 | B2 |   | 11/2009 | Wilcox et al. |
| 7,655,008 | B2 |   | 2/2010 | Lenke et al. |
| 7,794,464 | B2 |   | 9/2010 | Bridwell et al. |
| 7,794,476 | B2 |   | 9/2010 | Wisnewski |
| 7,914,536 | B2 |   | 3/2011 | MacDonald et al. |
| 7,922,731 | B2 |   | 4/2011 | Schumacher et al. |
| 8,034,089 | B2 |   | 10/2011 | Matthis et al. |

(Continued)

FOREIGN PATENT DOCUMENTS

EP        1590077      5/2010
WO     199002527      3/1990

(Continued)

*Primary Examiner* — Nicholas J Plionis

(57) ABSTRACT

A driver includes a sleeve having an inner surface defining a passageway. The sleeve extends along a longitudinal axis between a proximal end and an opposite distal end. The proximal end includes a groove in the inner surface. A biasing element is positioned partially in the groove. A shaft is disposed in the passageway. The shaft includes an outer surface, a first engagement portion, and a second engagement portion.

13 Claims, 9 Drawing Sheets

(56) References Cited

U.S. PATENT DOCUMENTS

| | | |
|---|---|---|
| 8,097,025 B2 | 1/2012 | Hawkes et al. |
| 8,157,806 B2 | 4/2012 | Frigg et al. |
| 8,167,910 B2 | 5/2012 | Nilsson |
| 8,197,518 B2 | 6/2012 | Hammill, Sr. et al. |
| 8,206,395 B2 | 6/2012 | McLean et al. |
| 8,277,453 B2 | 10/2012 | Kave et al. |
| 8,287,546 B2 | 10/2012 | King et al. |
| 8,298,265 B2 | 10/2012 | Purcell et al. |
| 8,298,275 B2 | 10/2012 | Rezach |
| 8,308,782 B2 | 11/2012 | Jackson |
| 8,394,109 B2 | 3/2013 | Hutton et al. |
| 8,460,294 B2 | 6/2013 | Overes |
| 8,491,582 B2 | 7/2013 | Keilen |
| 8,623,022 B2 | 1/2014 | Forton et al. |
| 8,900,237 B2 | 2/2014 | Ramsay et al. |
| 8,968,367 B2 | 3/2015 | Kretzer et al. |
| 9,066,762 B2 | 6/2015 | Jones et al. |
| 9,066,763 B2 | 6/2015 | Khoo et al. |
| 9,179,947 B2 | 11/2015 | Bass |
| 9,402,660 B2 | 8/2016 | Brinkman et al. |
| 9,795,370 B2 | 10/2017 | O'Connell et al. |
| 10,085,773 B2 | 10/2018 | Asaad et al. |
| 2003/0149341 A1 | 8/2003 | Clifton |
| 2004/0034298 A1 | 2/2004 | Johnson et al. |
| 2004/0210232 A1 | 10/2004 | Patel et al. |
| 2005/0021040 A1 | 1/2005 | Bertagnoli |
| 2005/0203532 A1 | 9/2005 | Ferguson et al. |
| 2007/0270839 A1 | 11/2007 | Jeon et al. |
| 2008/0119862 A1 | 5/2008 | Wicker et al. |
| 2008/0262494 A1 | 10/2008 | Moore et al. |
| 2010/0246923 A1 | 9/2010 | Nathaniel et al. |
| 2011/0083536 A1* | 4/2011 | Palmisano .............. B25B 15/02 81/439 |
| 2011/0093021 A1 | 4/2011 | Fanger et al. |
| 2013/0190823 A1 | 7/2013 | Thompson |
| 2014/0018816 A1* | 1/2014 | Fenn ................... A61B 17/162 606/104 |
| 2015/0051648 A1* | 2/2015 | May ................... A61B 17/7086 606/264 |
| 2017/0311987 A1 | 11/2017 | Bobbitt et al. |
| 2019/0029729 A1 | 1/2019 | Mire et al. |

FOREIGN PATENT DOCUMENTS

| | | |
|---|---|---|
| WO | 2004014231 | 2/2004 |
| WO | 2004066906 | 8/2004 |
| WO | 2005107415 | 11/2005 |
| WO | 2006094754 | 9/2006 |
| WO | 2006118998 | 11/2006 |
| WO | 2007092797 | 8/2007 |
| WO | 2008155772 | 12/2008 |

* cited by examiner

MULTI-PURPOSE SCREWDRIVER AND METHOD OF USE

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a driver includes a sleeve comprising an inner surface defining a passageway. The sleeve extends along a longitudinal axis between a proximal end and an opposite distal end. The proximal end comprises a groove in the inner surface, A biasing element is positioned partially in the groove. A shaft is disposed in the passageway. The shaft comprises an outer surface, a first engagement portion, and a second engagement portion. The sleeve is translatable relative to the shaft in an axial direction, along the longitudinal axis. The biasing element creates friction between the sleeve and shaft, limiting relative axial motion between the sleeve and shaft, when the biasing element engages the outer surface, the first engagement portion, and the second engagement portion. When the biasing element engages the outer surface, a first amount of translational force is required to overcome the friction to move the sleeve relative to the shaft axially. When the biasing element engages the first engagement portion, a second amount of translational force, greater than the first amount of translational force, is required to overcome the friction to move the sleeve relative to the shaft axially. When the biasing element engages the second engagement portion, a third amount of translational force, greater than the second amount of translational force, is required to overcome the friction to move the sleeve relative to the shaft axially In one embodiment, a surgical system includes a fastener comprising a threaded screw and a receiver that is configured to pivot relative to the screw in a plurality of planes. The screw defines a socket. The receiver comprises spaced apart arms that define an implant cavity therebetween, A driver comprises a sleeve including an inner surface defining passageway. The sleeve extends along a longitudinal axis between a proximal end and an opposite distal end. The proximal end comprises a groove that extends into the inner surface. A biasing element is positioned in the groove. A shaft is disposed in the passageway. The shaft comprises a proximal end defining a drive portion and a distal end defining a drive bit. The shaft comprises an outer surface, a first engagement portion, and a second engagement portion.

In one embodiment, a surgical method comprises the steps of positioning an end of a threaded screw of a fastener adjacent to tissue, the fastener comprising a receiver that is coupled to the screw and configured to pivot in a plurality of planes relative to the screw; positioning a drive bit of a shaft of a driver in a socket of the screw, the shaft comprising a biasing element positioned in a groove of a sleeve of the shaft, the biasing element engaging an outer surface of the shaft; translating the sleeve relative to the shaft such that the biasing element engages a first engagement portion of the shaft and opposite first and second flanges of the sleeve engage inner surfaces of arms of the receiver; translating the shaft relative to the sleeve such that the biasing element engages a second engagement portion of the shaft and the drive bit of the shaft disengages from the socket of the screw; and selectively pivoting the receiver relative to the screw using the sleeve.

BRIEF DESCRIPTION OF THE DRAWINGS

The present disclosure will become more readily apparent from the specific description accompanied by the following drawings, in which.

DETAILED DESCRIPTION

Figure 1:
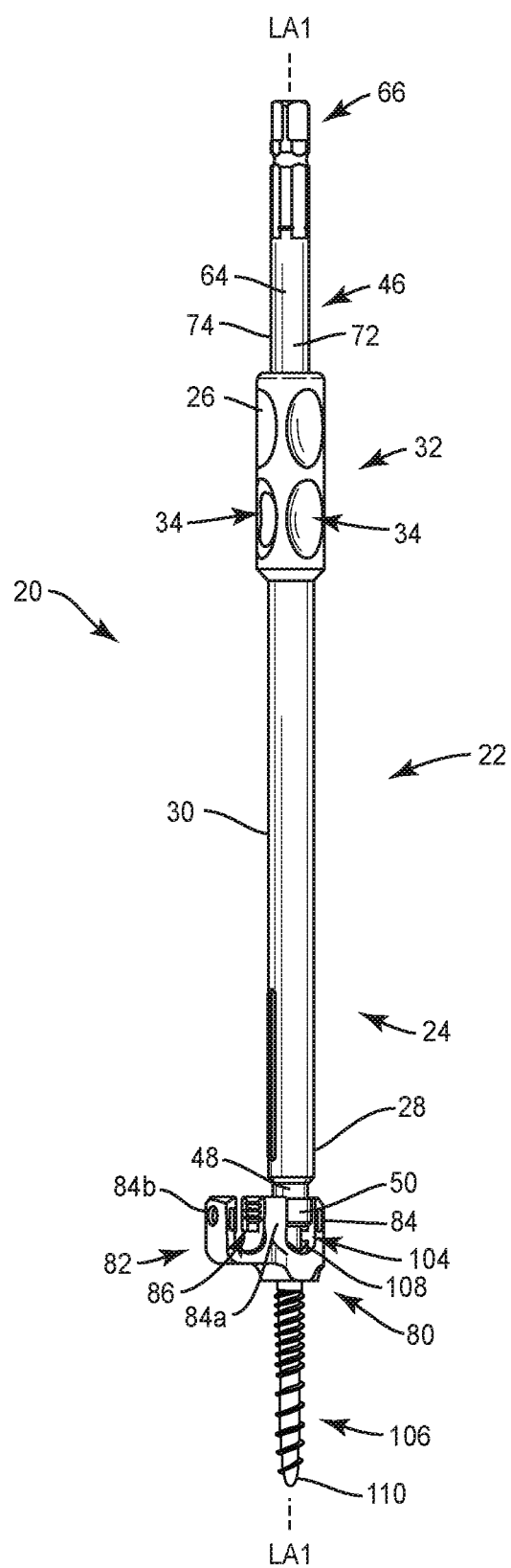
FIG. 1 is a side view of one embodiment of a surgical system, in accordance with principles of the present disclosure.
Figure 2:
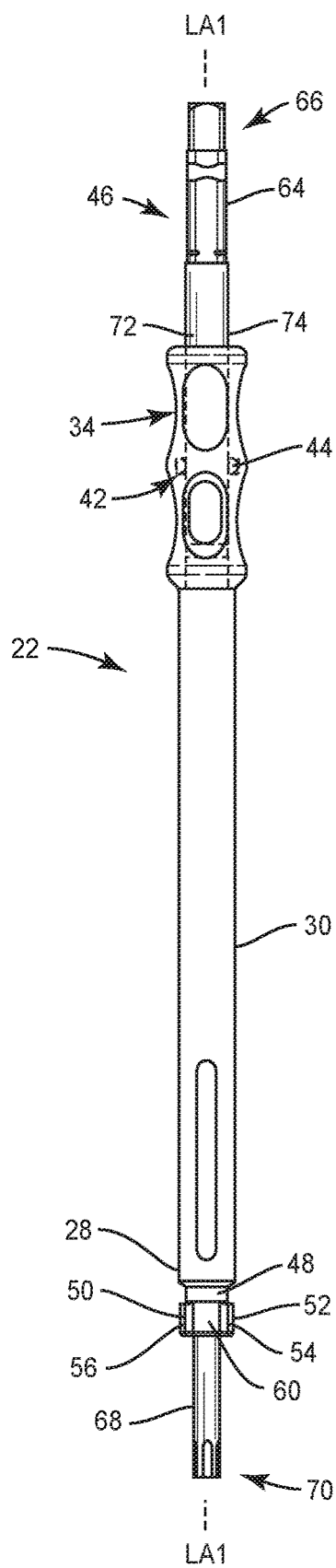
FIG. 2 is a side view, in part phantom, of components of the surgical system shown in FIG. 1 in a first mode/disposition.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, at a cervical, thoracic, lumbar and/or sacral region of a spine.

In some embodiments, the present surgical system includes a driver having a sleeve and inside shaft, for use in positioning and implanting an implant including a bone screw and a head. The sleeve and inside shaft can be manipulated independently of the other, allowing the user to control orientation of the head and the bone screw, selectively—both at the same time and independently. In some embodiments, the driver of the present surgical system overcomes limitations in conventional drivers that either lock the head in one orientation relative to the bone screw or do not control the head. The driver can be used to position the head without staying axial to the bone screw. In some embodiments, the driver of the present surgical system is configured for use with any of a variety of fasteners or screws, such as, for example, a multi-axial screw (MAS), a reduction multi-axial screw (RMAS), and a dual rod multi-axial screw (DRMAS) to reduce the number of instruments and simplify surgical flow. Indeed, there are currently different drivers for different screws. The driver of the present surgical system is configured for use with a plurality of different screws and hence would reduce or eliminate the need for additional drivers.

In some embodiments, the driver of the present surgical system is configured for use in three positions: load, drive, and head manipulation. In the load position or load range, the positioning sleeve can be locked out of the way for better visualization when engaging a driver shaft, such as a driver torx, with the bone screw. There is no one position in which the sleeve locks so that the sleeve will retain its position at any point within the load region of the shaft. In particular, friction between a biasing element (i.e. spring) and the shaft prevents movement while theres no applied force by the user. This locks the driver in this range. The sleeve can be positioned and hold its orientation to the shaft anywhere along this load range. In this position, the driver can also be used as a standard driver that does not engage the head. In the drive position, the driver shaft is engaged with the bone screw and the sleeve is engaged with the screw head so the bone screw can be driven while independently controlling the head rotation with the sleeve. In the head-manipulation position, the driver shaft is disengaged from the bone screw so that the user can orient the head of the screw in any plane after the bone screw has been implanted. This can be done without disengaging the instrument from the implant. In some embodiments, the head manipulation position also makes the driver essentially a "2 in 1" device, by which a surgeon can orient the head to be in line without the need for a separate instrument.

In some embodiments, the driver of the present surgical system includes a mechanism having a canted coil spring that sits in a groove of the sleeve, such as of an intermediate grip of the sleeve, and presses against the inner drive shaft. In a first mode, such as, for example, the load range mode, the spring presses against the inner drive shaft, creating friction with the inner drive shaft, by an amount that allows easy manual movement of the outer sleeve as desired, but causes the outer sleeve to stay in place otherwise. This allows the outer sleeve to be positioned anywhere within a range of (infinite) positions, which is helpful to allow for good and desired visualization in engaging the driver shaft with the bone screw. In a second mode, such as, for example, the drive position mode, a first recess of the inner drive shaft receives the spring, releasably locking the sleeve in that position—wherein the sleeve groove is aligned generally with the recess—for the driving function such that the driver shaft is engaged with the bone screw and the sleeve is engaged with the screw head. In a third mode, such as, for example, the head manipulation mode, the inner drive shaft includes a second recess spaced from the first recess for releasably locking the sleeve there, for a head manipulation function.

In some embodiments, one or all of the components of the surgical system may be disposable, peel-pack, pre-packed sterile devices. In some embodiments, the components of the surgical system are configured for one time use and are disposed after they are used one time. However, it is contemplated that one or all of the components of the surgical system may be reusable. The surgical system may be configured as a kit with multiple sized and configured components. In some embodiments, one or more of the components of the surgical system are configured to be sterilized.

In some embodiments, the disclosed drivers, surgical methods and systems may be alternatively employed in a surgical treatment with a patient in a prone or supine position, and/or employ various surgical approaches, including anterior, posterior, posterior mid-line, direct lateral, postero-lateral, antero-lateral approaches, etc., in any body region. The drivers, methods and systems of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which font a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, references to "upper" and "lower" would be relative and used only in context to the other, and are not necessarily "superior" and "inferior."

Further, as used in the specification and including the appended claims, "treating" or "treatment" of a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-12, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 includes a driver 22 comprising a positioning sleeve, such as, for example, a sleeve 24 that extends along a longitudinal axis LA1 between a proximal end 26 and an opposite distal end 28. Sleeve 24 comprises a tubular shaft 30 that extends between end 26 and end 28. In various embodiments, end 26 includes an intermediate grip, such as, for example, a grip 32. In some embodiments, grip 32 has a maximum diameter that is greater than a maximum diameter of shaft 30 to facilitate grasping of the sleeve by a user. In some embodiments, grip 32 is shaped to facilitate grasping of grip 32, such as by including a plurality of spaced apart protrusions and/or cavities 34. In some embodiments, cavities 34 are radially disposed about a circumference of grip 32. In some embodiments, cavities 34 are disposed two or more rows and/or two or more columns to provide a secure grip and thereby reduce user fatigue. In some embodiments, an outer surface of grip 32 may have various surface configurations to enhance gripping, such as, for example, rough, arcuate, undulating, porous, semi-porous, dimpled, polished and/or textured according to the requirements of a particular application.

Figure 3:
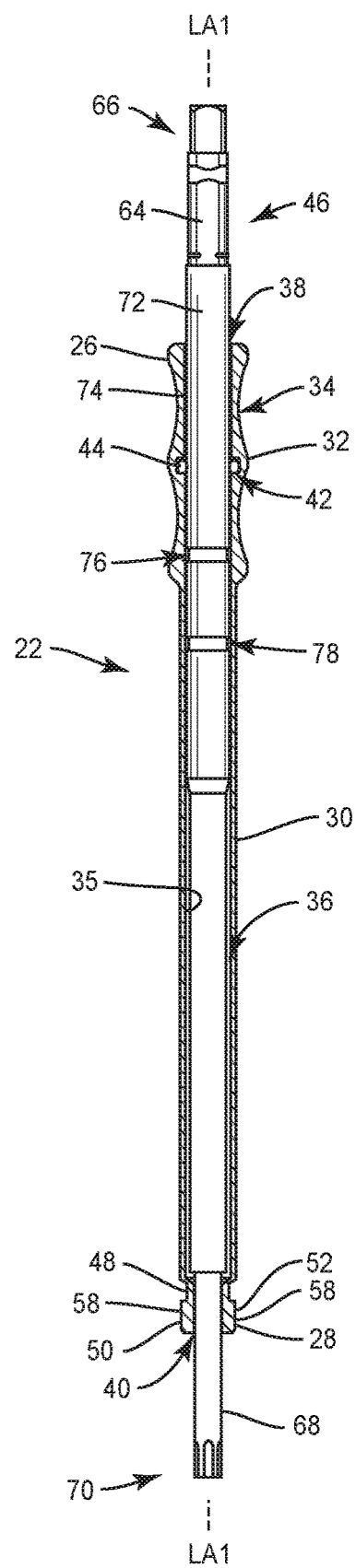
FIG. 3 is a side, cross sectional view of components of the surgical system shown in FIG. 1 in the first mode/disposition.
Figure 5:
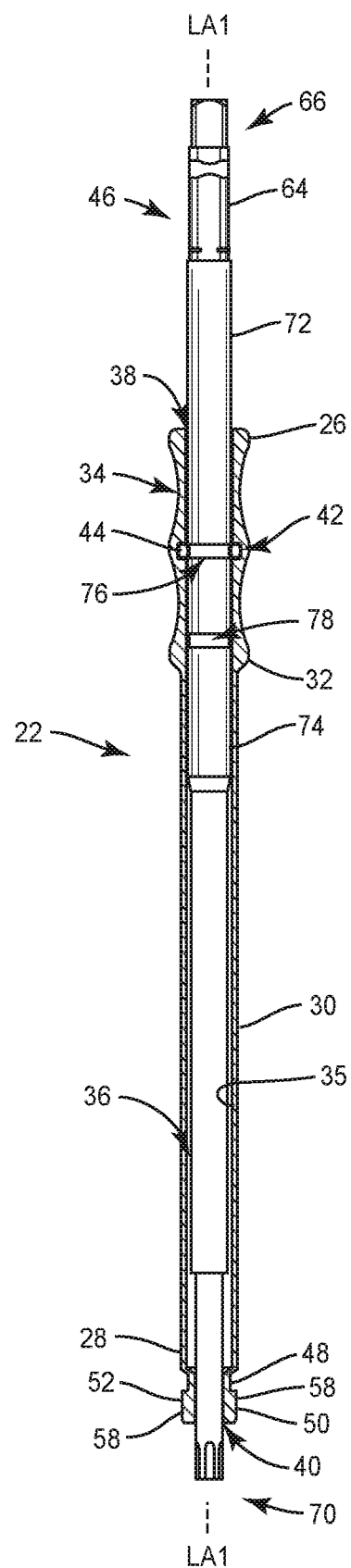
FIG. 5 is a side, cross sectional view of components of the surgical system shown in FIG. 1 in the second mode/disposition.
Figure 7:
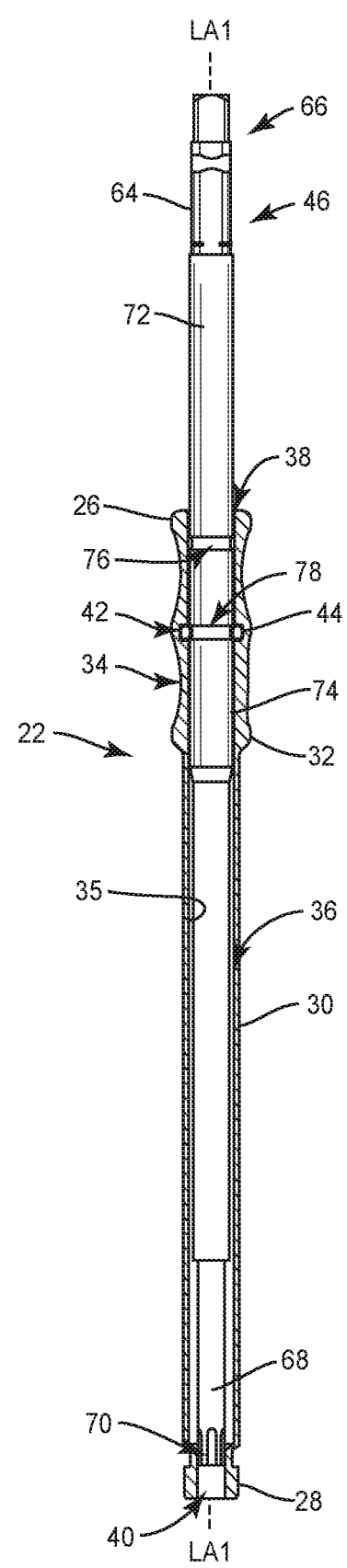
FIG. 7 is a side, cross sectional view of components of the surgical system shown in FIG. 1 in the third mode/disposition.

Sleeve 24 includes an inner surface 35 defining passageway 36 that extends the entire length of sleeve 24, as shown in FIGS. 3, 5 and 7, for example. End 26 includes an opening 38 and end 28 includes an opening 40. Openings 38, 40 are in communication with passageway 36. In some embodiments, passageway 36 and openings 38, 40 each extend parallel to axis LA1. In some embodiments, opening 40 is coaxial with opening 38. In some embodiments, passageway 36 and openings 38, 40 may be disposed at alternate orientations, relative to axis LA1, such as, for example, transverse, perpendicular and/or other angular orientations such as acute or obtuse, co-axial and/or may be offset or staggered. In some embodiments, passageway 36 and/or openings 38, 40 have a uniform diameter along the entire length thereof. In some embodiments, passageway 36 and/or openings 38, 40 may have various cross section configurations, such as, for example, oval, oblong, triangular, rectangular, square, polygonal, irregular, uniform, non-uniform, variable, tubular and/or tapered.

End 26 comprises a circumferential groove 42 that extends into surface 35. The groove 42 in various embodiments does not extend through the sleeve wall to an opposite outer surface of sleeve 24. A biasing element 44, such as, for example, a spring is positioned in groove 42. In some embodiments, spring 44 is a coil spring. In some embodiments, spring 44 is a canted coil spring. In some embodiments, spring 44 is a BAL SPRING® coil spring, available from Bal Seal Engineering, Inc. in Foothill Ranch, Calif.

Driver 22 includes an inside shaft, such as, for example, a shaft 46 having an end configured for disposal in an implant and an end configured to engage an actuator to rotate shaft 46 to drive the implant into tissue, such as, for example, bone, as discussed herein. Spring 44 is configured for engagement with shaft 46 and sleeve 24 in various configurations, specifically between first, second and third positions, as discussed herein.

Figure 8:
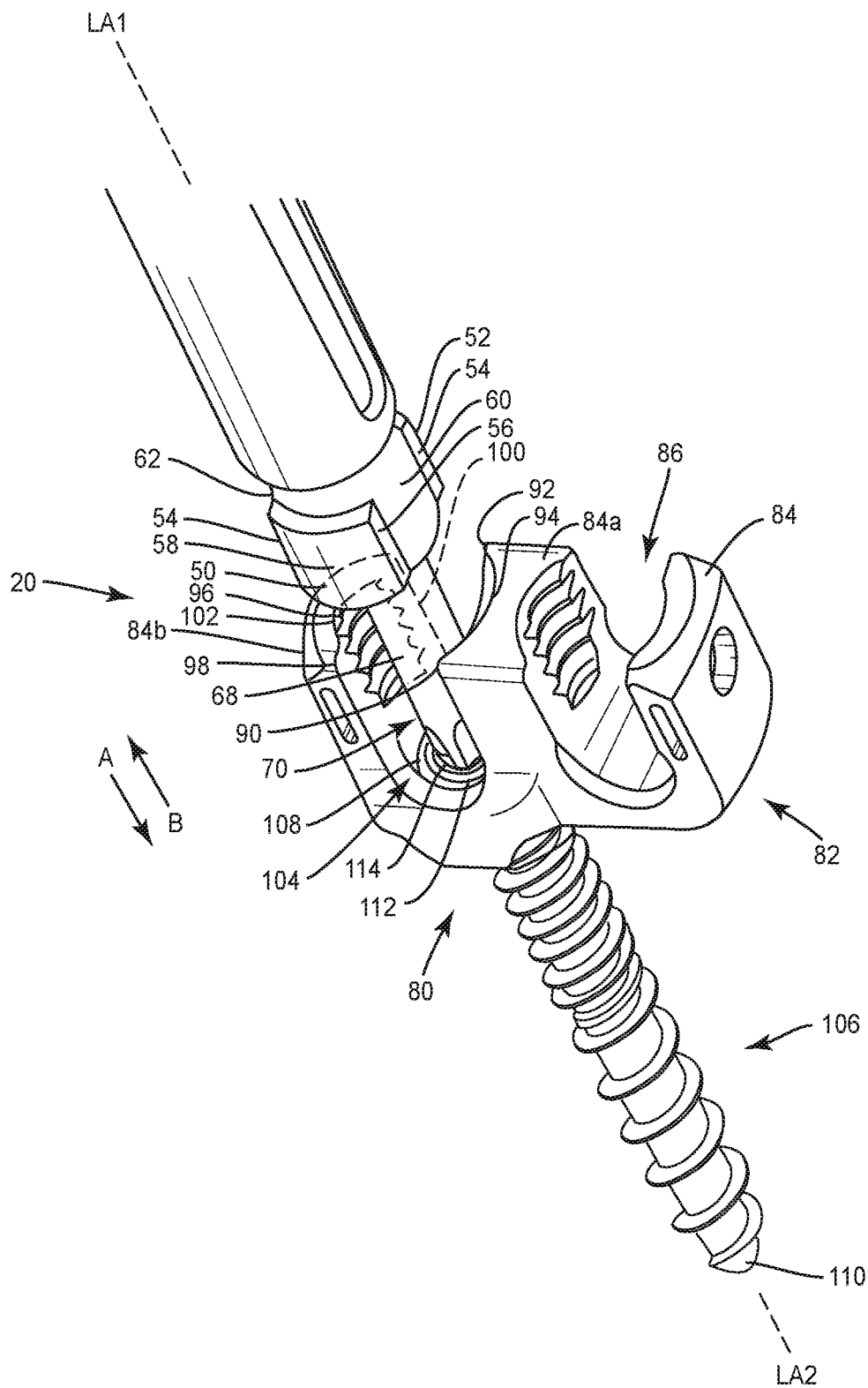
FIG. 8 is a perspective view of components of the surgical system shown in FIG. 1.
Figure 9:
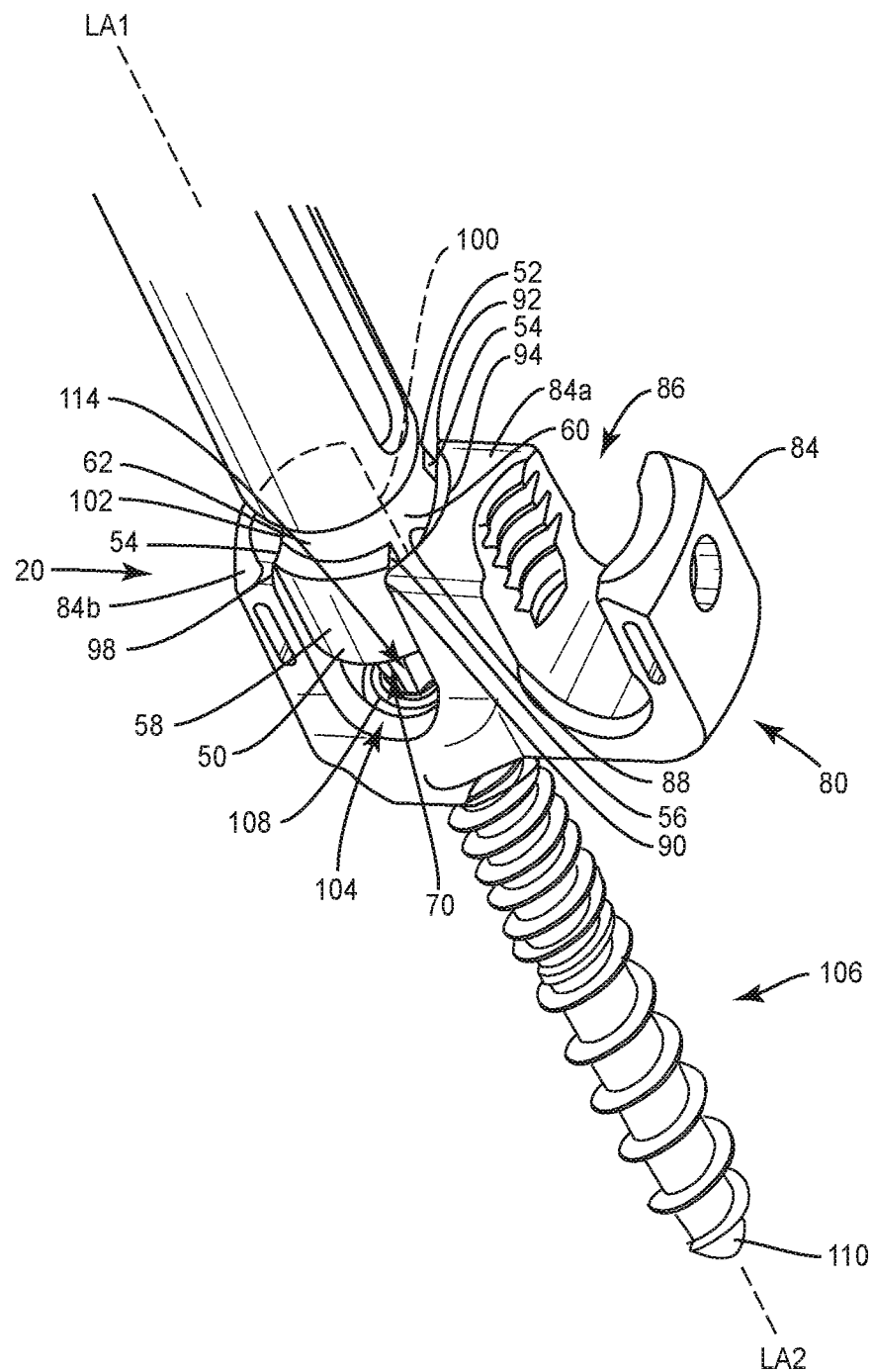
FIG. 9 is a perspective view of components of the surgical system shown in FIG. 1.
Figure 10:
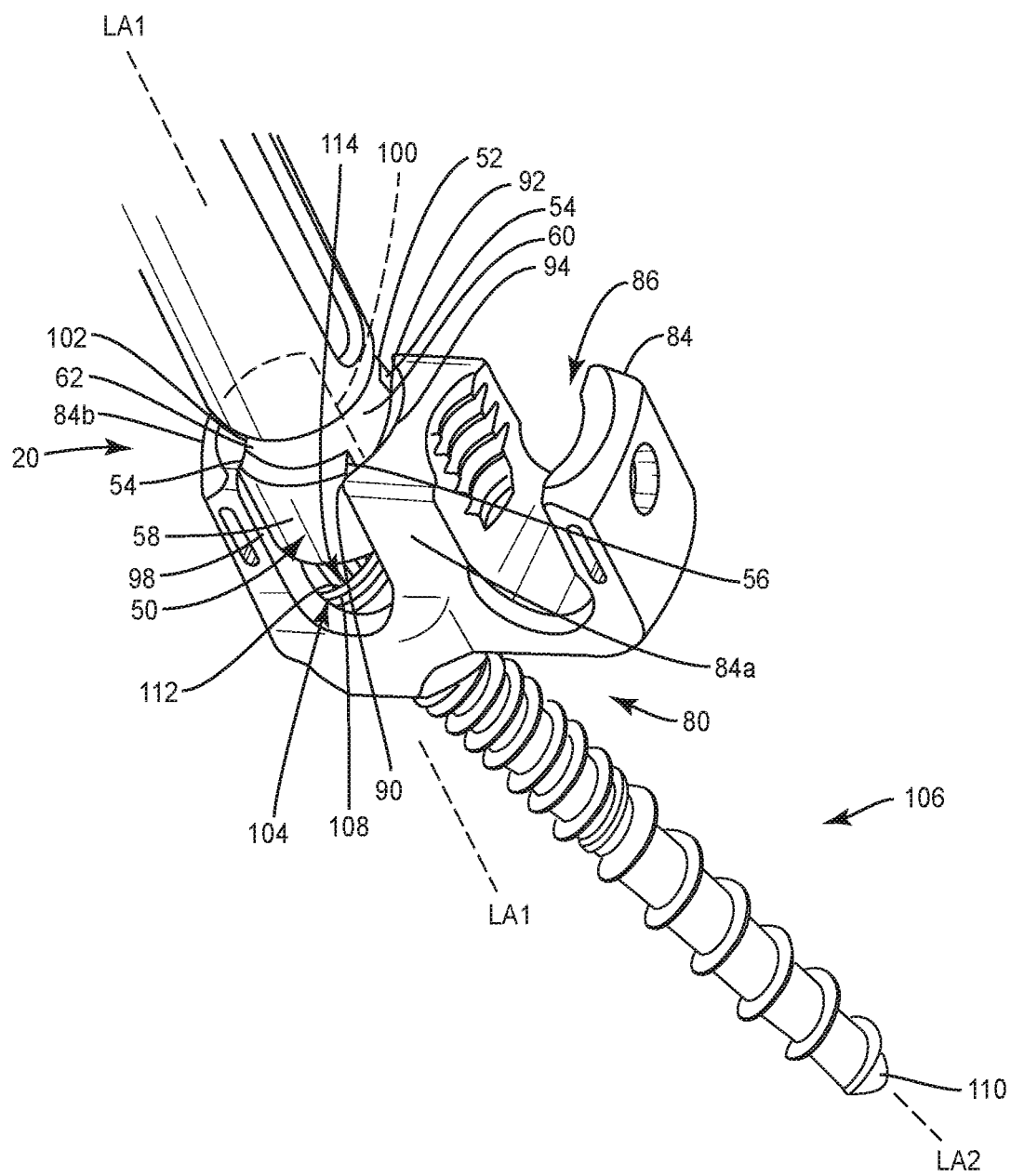
FIG. 10 is a perspective view of components of the surgical system shown in FIG. 1.
Figure 11:
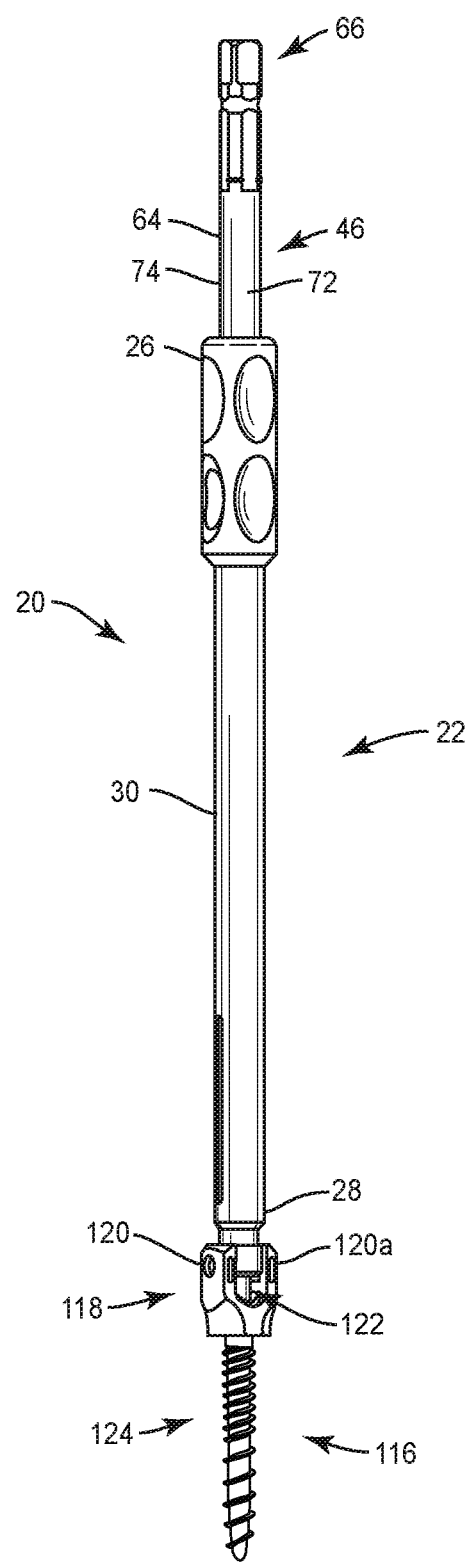
FIG. 11 is a side view of one embodiment of components of the surgical system shown in FIG. 1, in accordance with the present principles of the present disclosure.

In various embodiments, end 28 includes a cylindrical portion 48 having a maximum outer diameter that is less than a maximum outer diameter of shaft 30. A flange, such as, for example, a lug 50 extends outwardly from a first side of portion 48 and a flange, such as, for example, a lug 52 extends from an opposite, second side of portion 48. Lugs 50, 52 each include an end surface 54, an opposite end surface 56 and an outer surface 58 that is in some embodiments convexly curved from surface 54 to surface 56, as best shown in FIGS. 8-10. Surface 56 of lug 50 is in some embodiments spaced apart from surface 54 of lug 52 by an arcuate outer surface 60 of portion 48 and surface 54 of lug 50 is spaced apart from surface 56 of lug 52 by an arcuate outer surface 62 of portion 48. In some embodiments, surfaces 54, 56 are entirely planar and extend parallel to axis LA1. In some embodiments, surface 60 is convexly curved from surface 56 of lug 50 to surface 54 of lug 52 and surface 62 is convexly curved from surface 54 of lug 50 to surface 56 of lug 52. In some embodiments, surface 60 has a continuous radius of curvature from surface 56 of lug 50 to surface 54 of lug 52 and surface 62 has a continuous radius of curvature from surface 54 of lug 50 to surface 56 of lug 52. Lugs 50, 52 are configured for engagement with an implant, such as, for example, a bone fastener 80 (FIG. 8), and particularly with a head receiver 82 of the fastener, to connect sleeve 24 with the bone fastener, as discussed herein.

Shaft 46 is disposed in passageway 36 and extends between a proximal end 64 defining a drive portion 66 and a distal end 68 defining a drive bit 70. Shaft 46 is coaxial with axis LA1 when shaft 46 is disposed in passageway 36. Drive portion 66 is configured for engagement with an actuator, as described herein, to rotate shaft 46 relative to sleeve 24 about axis LA1, as discussed herein. In some embodiments, drive portion 66 may include a square, triangular, polygonal, star or hexalobe cross sectional configuration configured engage a correspondingly shaped portion of the actuator. In some embodiments, drive bit 70 may include a square, triangular, polygonal, star or hexalobe cross sectional configuration configured engage a correspondingly shaped socket of a bone fastener, as discussed herein.

Shaft 46 is part of or connected to a shaft 72 having an outer surface 74 defining one or a plurality of engagement portions. For example, in some embodiments, shaft 74 comprises a recess, such as, for example, a first engagement portion 76 that extends into surface 74 and a recess, such as, for example, a second engagement portion 78 that extends into surface 74. Engagement portion 76 is spaced apart from engagement portion 78 along a length of shaft 72. Spring 44 is configured for engagement with surface 74 to orient sleeve 24 relative to shaft 46 in the first position shown in FIGS. 2 and 3, as discussed herein. Engagement portion 76 is in various embodiments a circumferential recess configured for disposal of spring 44 to orient sleeve 24 relative to shaft 46 in the second position shown in FIGS. 4 and 5, as discussed herein. Engagement portion 78 is in various embodiments a circumferential recess configured for disposal of spring 44 to orient sleeve 24 relative to shaft 46 in the third position shown in FIGS. 6 and 7, as discussed herein.

Driver 22 is configured for engagement with a bone fastener, such as, for example, a bone fastener 80. In some embodiments, fastener 80 is the same or similar to any of the fasteners disclosed in U.S. patent application Ser. No. 15/139,395, filed on Aug. 25, 2015, which is expressly incorporated by reference herein, in its entirety. Fastener 80 is in some cases a DRMAS configured for engagement with tissue and includes a receiver 82. Receiver 82 includes spaced apart arms 84, 84a, 84b. Arms 84, 84a include an inner surface that defines a U-shaped passageway 86. The surfaces that define passageway 86 each include a thread form configured for engagement with a set screw. The set screw can be threaded with arms 84, 84a to attach, fix and/or lock an implant, such as, for example, a spinal rod with receiver 82, as described herein. Arm 84a includes an inner surface 88 having a planar portion 90 that is spaced apart from a planar portion 92 by an arcuate portion 94, as best shown in FIGS. 8-10. Portions 90, 92, 94 are configured for engagement with surface 56 of lug 50, surface 54 of lug 52 and surface 60 of portion 48, respectively, to couple sleeve 24 to receiver 82, as shown in FIGS. 9 and 10. In some embodiments, portion 94 is convexly curved from portion 90 to portion 92. In some embodiments, portion 94 has a continuous radius of curvature from portion 90 to portion 92. Arm 84b includes an inner surface 96 having a planar portion 98 that is spaced apart from a planar portion 100 by an arcuate portion 102, as best shown in FIGS. 8-10. Portions 98, 100, 102 are configured for engagement with surface 54 of lug 52, surface 56 of lug 50 and surface 62 of portion 48, respectively, to couple sleeve 24 to fastener 80, as shown in FIGS. 9 and 10. In some embodiments, portion 102 is convexly curved from portion 98 to portion 100. In some embodiments, portion 102 has a continuous radius of curvature from portion 98 to portion 100. Spaced apart arms 84a, 84b define a U-shaped passageway 104 disposed adjacent to passageway 86. Surfaces 88, 96 each include a thread form configured for engagement with a set screw to attach, fix and/or lock a second implant, such as, for example, a second spinal rod, with receiver 82.

Fastener 80 includes a threaded screw 106 configured for penetrating tissue. Screw 106 extends along a longitudinal axis LA2 between a proximal head 108 and a distal tip 110. Head 108 includes an inner surface 112 defining a socket 114 configured for disposal of drive bit 70 to rotate screw 106 about axis LA2, as discussed herein. In some embodiments, socket 114 may include a square, triangular, polygonal, star or hexalobe cross sectional configuration configured engage a correspondingly shape socket of drive bit 70, as discussed herein. Head 108 is positioned in an opening in receiver 82 such that screw 106 is pivotable relative to receiver 82 in a plurality of planes. In some embodiments, screw 106 has an external thread form that may include a single thread or a plurality of discrete threads. In some embodiments, other engaging structures may be located on screw 106, such as, for example, a nail configuration, barbs, expanding elements, raised elements and/or spikes to facilitate engagement of screw 106 with tissue.

In assembly, operation and use, access to a surgical site is obtained and a particular surgical procedure is performed. The components of surgical system 20, driver 22 and fastener 80 are employed to augment the surgical treatment. For example, tip 110 of screw 106 is positioned adjacent to tissue, such as, for example, bone, with receiver 82 coupled to screw 106, as discussed herein. Driver 22 is delivered to surgical site with sleeve 24 oriented relative to shaft 46 in the first position (FIGS. 2 and 3) to allow for visualization of drive bit 70. That is, when sleeve 24 is in the first position, portion 60 of sleeve 24 is sufficiently spaced apart from drive bit 70 to allow visualization, by a user or vision system, of drive bit 70, as shown in FIG. 8. When sleeve 24 is in the first position, spring 44 directly engages surface 74 between engagement portion 76 and drive portion 66. It is envisioned that spring 44 can engage surface 74 anywhere between engagement portion 76 and drive portion 66 when sleeve 24 is in the first position. Spring 44 creates a first amount of friction with shaft 72 that provisionally fixes sleeve 24 relative to shaft 46 such that rotation of shaft 46 relative to sleeve 24 about axis LA1 and translation of shaft 46 relative to sleeve 24 along axis LA1 is prevented. That is, a first amount of force is required to overcome the first amount of friction to avow rotation of shaft 46 relative to sleeve 24 about axis LA1 and translation of shaft 46 relative to sleeve 24 along axis LA1. Drive bit 70 is inserted into socket 114 such that axis LA1 is parallel and/or coaxial with axis LA2, as shown in FIG. 8.

In some embodiments, at least the first amount of force is applied to sleeve 24 to move sleeve 24 relative to shaft 46 along axis LA1 in the direction shown by arrow A in FIG. 8 and/or the direction shown by arrow B in FIG. 8 to overcome the first amount of friction to allow rotation of shaft 46 relative to sleeve 24 about axis LA1. A motorized and/or manual actuator, such as, for example, a human hand, is engaged with drive portion 66 to connect the actuator to shaft 46. The actuator can be connected with shaft 46 either before or after drive bit 70 is inserted into socket 114, depending on a particular surgical procedure. The actuator causes shaft 46 to rotate relative to sleeve 24 such that shaft 46 rotates screw 106 to drive screw 106 into the tissue.

Figure 4:
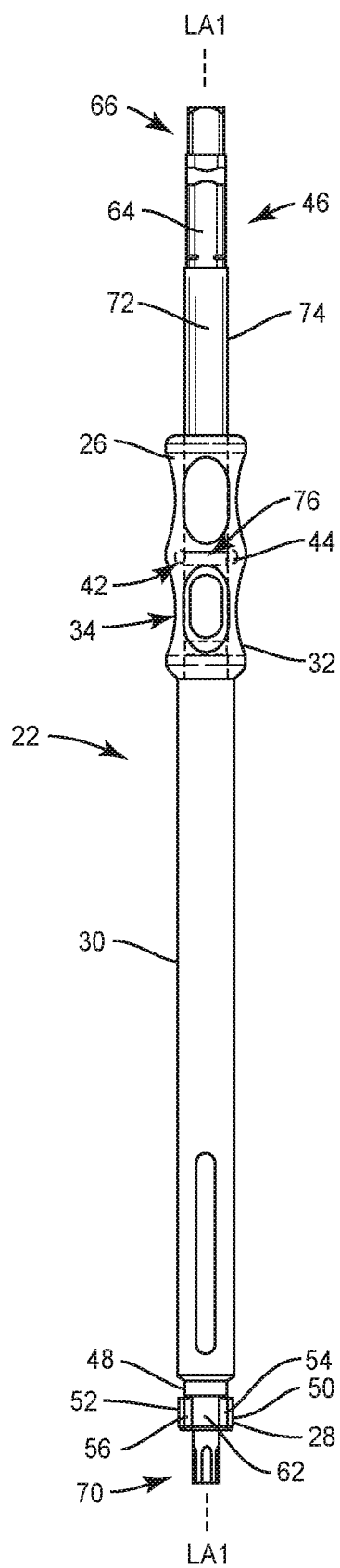
FIG. 4 is a side view, in part phantom, of components of the surgical system shown in FIG. 1 in a second mode/disposition.

In some embodiments, at least the first amount of force is applied to sleeve 24 to move sleeve 24 relative to shaft 46 along axis LA1 in the direction shown by arrow A in FIG. 8 to overcome the first amount of friction. Sleeve is translated relative to shaft 46 along axis LA1 in the direction shown by arrow A in FIG. 8 until spring 44 is positioned in engagement portion 76, as shown in FIGS. 4 and 5, and portion 60 of sleeve 24 is positioned in passageway 104, as shown in FIG. 9 to orient sleeve 24 relative to shaft 46 in the second position. In particular, sleeve 24 is positioned in passageway 104 such that surface 56 of lug 50 directly engages portion 90, surface 54 of lug 52 directly engages portion 92, surface 60 directly engages portion 94, surface 54 of lug 50 directly engages portion 98, surface 56 of lug 52 directly engages portion 100 and surface 62 directly engages portion 102, as shown in FIG. 9, to prevent rotation of receiver 82 relative to sleeve 24. Drive bit 70 remains inserted into socket 114 when sleeve 24 is in the second position such that axis LA1 is parallel and/or coaxial with axis LA2, as shown in FIG. 9. When sleeve 24 is in the second position, spring 44 is positioned in engagement portion 76 such that spring 44 creates a second amount of rotational friction and a second amount of translational friction with shaft 72. That is, sleeve 24 can be freely rotated 360 degrees relative to shaft 46 about axis LA1 and translation of shaft 46 relative to sleeve 24 along axis LA1 is provisionally prevented. A second amount of translational force is required to disengage spring 44 from engagement portion 76 to allow translation of shaft 46 relative to sleeve 24 along axis LA1. The second amount of rotational friction is less than the first amount of rotational friction, the second amount of translational friction is greater than or equal to the first amount of translational friction, and the second amount of translational force is greater than or equal to the first amount of translational force. A motorized and/or manual actuator is engaged with drive portion 66 to connect the actuator to shaft 46 while a second motorized and/or manual actuator is engaged with grip 32. The first actuator rotates shaft 46 relative to sleeve 24 about axis LA1 such that shaft 46 rotates screw 106 about axis LA2 to drive screw 106 into the tissue while the second actuator rotates and/or maintains the orientation of sleeve 24 and, with it, receiver 82, about axis LA1.

Figure 6:
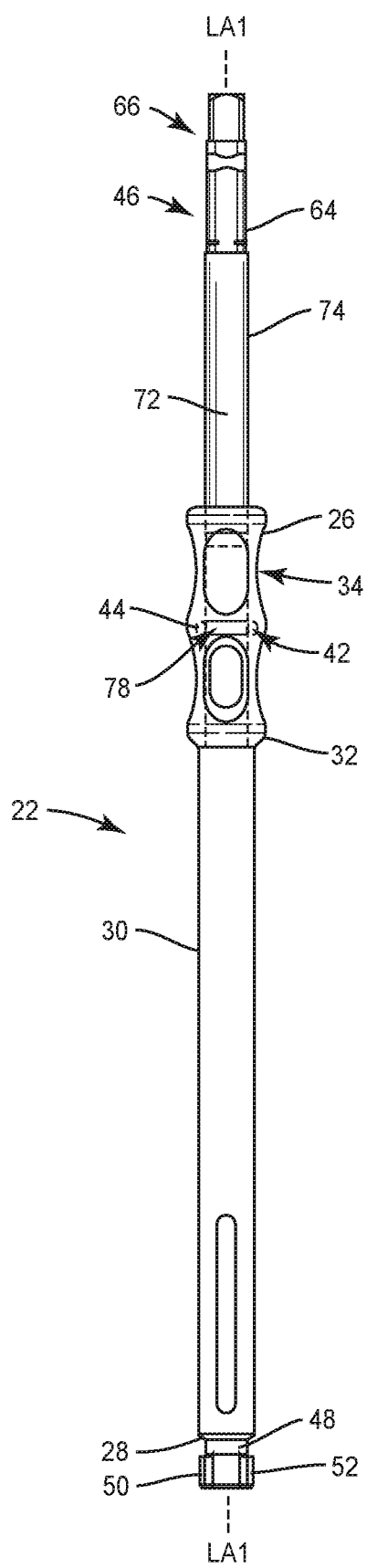
FIG. 6 is a side view, in part phantom, of components of the surgical system shown in FIG. 1 in a third mode/disposition.

Once screw 106 is sufficiently driven into the tissue to fix screw 106 relative to the tissue, at least the second amount of translational force is applied to shaft 46 to move shaft 46 relative to sleeve 24 along axis LA1 in the direction shown by arrow B in FIG. 8 to overcome the second amount of translational friction. Shaft 46 is translated relative to sleeve 24 along axis LA1 in the direction shown by arrow B in FIG. 8 until spring 44 is positioned in engagement portion 78, as shown in FIGS. 6 and 7, which orients sleeve 24 relative to shaft 46 in the third position, as shown in FIG. 10. As sleeve 24 moves from the second position to the third position, drive bit 70 moves out of socket 114 and into passageway 36 such that drive bit 70 is positioned entirely within passageway 36, as shown in FIG. 7. Removal of drive bit 70 from socket 114 allows receiver 82 to pivot relative to screw 106 in one or a plurality of planes. Portion 48 remains positioned in passageway 104 such that surface 56 of lug 50 directly engages portion 90, surface 54 of lug 52 directly engages portion 92, surface 60 directly engages portion 94, surface 54 of lug 50 directly engages portion 98, surface 56 of lug 52 directly engages portion 100 and surface 62 directly engages portion 102 to prevent rotation of receiver 82 relative to sleeve 24.

In some embodiments, portion 48 is removed from passageway 104 and drive bit 70 is removed from socket 114 to disengage driver 22 from fastener 80 without orienting shaft 46 relative to sleeve 24 in the third position. For example, if passageway 86 and/or passageway 104 is/are properly oriented for engagement and/or disposal of an implant, such as, for example, one or more spinal rods, receiver 82 is not pivoted relative to screw 106 prior to disengaging driver 22 from fastener 80. In some embodiments, receiver 82 is pivoted relative to screw 106 using driver 22 such that axis LA1 extends transverse to axis LA2 prior to removing portion 48 from passageway 104, as shown in FIG. 10, to selectively orient passageway 86 and/or passageway 104 relative to screw 106 for engagement and/or disposal of an implant, such as, for example, one or more spinal rods, using driver 22. Once passageway 86 and/or passageway 104 is/are selectively oriented relative to screw 106, portion 48 is removed from passageway 104 to disengage driver 22 from receiver 82. Driver 22 is then removed from the surgical site. In some embodiments, an implant, such as, for example, one or more spinal rods, is/are positioned in passageway 86 and/or passageway 104 and a coupling element, such as, for example, a set screw is threaded with the threads of arms 84, 84a and/or the threads of arms 84a, 84b such that the set screw directly engages the implant(s) disposed in passageway 86 and/or passageway 104 to fix the implant(s) relative to receiver 82.

As discussed herein, driver 22 is adapted for use with a plurality of bone fasteners. That is, driver 22 can be used to drive screws of fasteners other than fastener 80 into tissue. For example, in one embodiment, shown in FIG. 11, surgical system 20 includes a bone fastener 116 that is similar to fastener 80. In some embodiments, fastener 116 is the same or similar to one of the fasteners disclosed in U.S. patent application Ser. No. 15/139,395, filed on Aug. 25, 2015, which is expressly incorporated by reference herein, in its entirety. Fastener 116 is a MAS configured for engagement with tissue and includes a receiver 118 having a pair of spaced apart arms 120, 120*a*. Receiver 118 is configured for engagement with driver 22, as described herein. Arms 120, 120*a* include an inner surface that defines a U-shaped passageway 122. Passageway 122 is configured for disposal of portion 48 to couple driver 22 to receiver 118. In some embodiments, all or only a portion of passageway 122 may have alternate cross section configurations, such as, for example, oval, oblong, triangular, square, polygonal, irregular, uniform, non-uniform, offset, staggered, and/or tapered. In some embodiments, arms 120, 120*a* may be disposed at alternate orientations, relative to a longitudinal axis of fastener 116, such as, for example, transverse, perpendicular and/or other angular orientations such as acute or obtuse, co-axial and/or may be offset or staggered. The inner surface of receiver 118 includes a thread form configured for engagement with a set screw. The set screw may be threaded with receiver 118 to attach, fix and/or lock an implant, such as, for example, a spinal rod with fastener 116 to facilitate connection of the tissue with surgical instruments for correction treatment, as described herein.

Fastener 116 includes a screw 124 configured for penetrating tissue, A head of screw 124 is positioned in an opening of receiver 118 such that screw 124 is rotatable relative to receiver 118 in a plurality of planes. The head of screw 124 includes a socket that is the same or similar to socket 114. Screw 124 has a cylindrical cross-sectional configuration and includes an outer surface having an external thread form. In some embodiments, the external thread form may include a single thread or a plurality of discrete threads. In some embodiments, other engaging structures may be located on screw 124, such as, for example, a nail configuration, barbs, expanding elements, raised elements and/or spikes to facilitate engagement of screw 124 with tissue. In some embodiments, all or only a portion of screw 124 may have alternate cross section configurations, such as, for example, oval, oblong, triangular, square, polygonal, irregular, uniform, non-uniform, offset, staggered, undulating, arcuate, variable and/or tapered. In some embodiments, the outer surface of screw 124 may include one or a plurality of openings. In some embodiments, all or only a portion of the outer surface of screw 124 may have alternate surface configurations to enhance fixation with tissue, such as, for example, rough, arcuate, undulating, mesh, porous, semi-porous, dimpled and/or textured. In some embodiments, all or only a portion of screw 124 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of screw 124 may be cannulated.

In assembly, operation and use, access to a surgical site is obtained and a particular surgical procedure is performed. The components of surgical system 20, driver 22 and fastener 116 are employed to augment the surgical treatment. For example, a tip of screw 124 is positioned adjacent to tissue, such as, for example, bone, with receiver 118 coupled to screw 124, as discussed herein. Driver 22 is delivered to surgical site with sleeve 24 oriented relative to shaft 46 in the first position (FIGS. 2 and 3) to allow for visualization of drive bit 70. Drive bit 70 is inserted into the socket in screw 124 such that axis LA1 is parallel and/or coaxial with an axis defined by screw 124.

A motorized and/or manual actuator is engaged with drive portion 66 to connect the actuator to shaft 46. The actuator can be connected with shaft 46 either before or after drive bit 70 is inserted into the socket in screw 124, depending on a particular surgical procedure. The actuator causes shaft 46 to rotate relative to sleeve 24 such that shaft 46 rotates screw 124 to drive screw 124 into the tissue.

In some embodiments, at least the first amount of force is applied to sleeve 24 to move sleeve 24 relative to shaft 46 along axis LA1 in the direction shown by arrow A in FIG. 8 to overcome the first amount of friction. Sleeve is translated relative to shaft 46 along axis LA1 in the direction shown by arrow A in FIG. 8 until spring 44 is positioned in engagement portion 76, as shown in FIGS. 4 and 5, and portion 60 of sleeve 24 is positioned in passageway 122 to orient sleeve 24 relative to shaft 46 in the second position. In some embodiments, sleeve 24 is positioned in passageway 122 in the same or similar manner as sleeve is positioned in passageway 104, as discussed herein. For example, surfaces of lugs 50, 52 and surfaces 60, 62 can engage surfaces of receiver 118 that are the same or similar to portion 90, portion 92, portion 94, portion 98, portion 100 and portion 102 to prevent rotation of receiver 118 relative to sleeve 24. Drive bit 70 remains inserted into the socket in screw 124 when sleeve 24 is in the second position such that axis LA1 is parallel and/or coaxial with the axis defined by screw 124. A motorized and/or manual actuator is engaged with drive portion 66 to connect the actuator to shaft 46 while a second motorized and/or manual actuator is engaged with grip 32. The first actuator rotates shaft 46 relative to sleeve 24 such that shaft 46 rotates screw 124 to drive screw 124 into the tissue while the second actuator rotates and/or maintains the orientation of sleeve 24 and with it, receiver 118 about axis LA1.

Once screw 124 is sufficiently driven into the tissue to fix screw 124 relative to the tissue, at least the second amount of translational force is applied to shaft 46 to move shaft 46 relative to sleeve 24 along axis LA1 in the direction shown by arrow B in FIG. 8 to overcome the second amount of translational friction. Shaft 46 is translated relative to sleeve 24 along axis LA1 in the direction shown by arrow B in FIG. 8 until spring 44 is positioned in engagement portion 78, as shown in FIGS. 6 and 7, which orients sleeve 24 relative to shaft 46 in the third position. As sleeve 24 moves from the second position to the third position, drive bit 70 moves out of the socket in screw 124 and into passageway 36 such that drive bit 70 is positioned entirely within passageway 36, as shown in FIG. 7, Removal of drive bit 70 from the socket in screw 124 allows receiver 118 to pivot relative to screw 124 in one or a plurality of planes. Portion 48 remains positioned in passageway 122 to prevent rotation of receiver 118 relative to sleeve 24.

In some embodiments, portion 48 is removed from passageway 122 and drive bit 70 is removed from the socket in screw 124 to disengage driver 22 from fastener 116 without orienting shaft 46 relative to sleeve 24 in the third position. For example, if passageway 122 is properly oriented for engagement and/or disposal of an implant, such as, for example, one or more spinal rods, receiver 118 is not pivoted relative to screw 124 prior to disengaging driver 22 from fastener 116. In some embodiments, receiver 118 is pivoted relative to screw 124 using driver 22 such that axis LA1 extends transverse to the axis defined by screw 124 prior to removing portion 48 from passageway 122 to selectively orient passageway 122 relative to screw 124 for engagement and/or disposal of an implant, such as, for example, one or more spinal rods, using driver 22. Once passageway 122 is selectively oriented relative to screw 124, portion 48 is removed from passageway 122 to disengage driver 22 from receiver 118. Driver 22 is then removed from the surgical site. In some embodiments, an implant, such as, for example, one or more spinal rods, is/are positioned in passageway 122 and a coupling element, such as, for example, a set screw is threaded with the threads of arms 120, 120*a* such that the set screw directly engages the implant(s) disposed in passageway 122 to fix the implant(s) relative to receiver 118.

Figure 12:
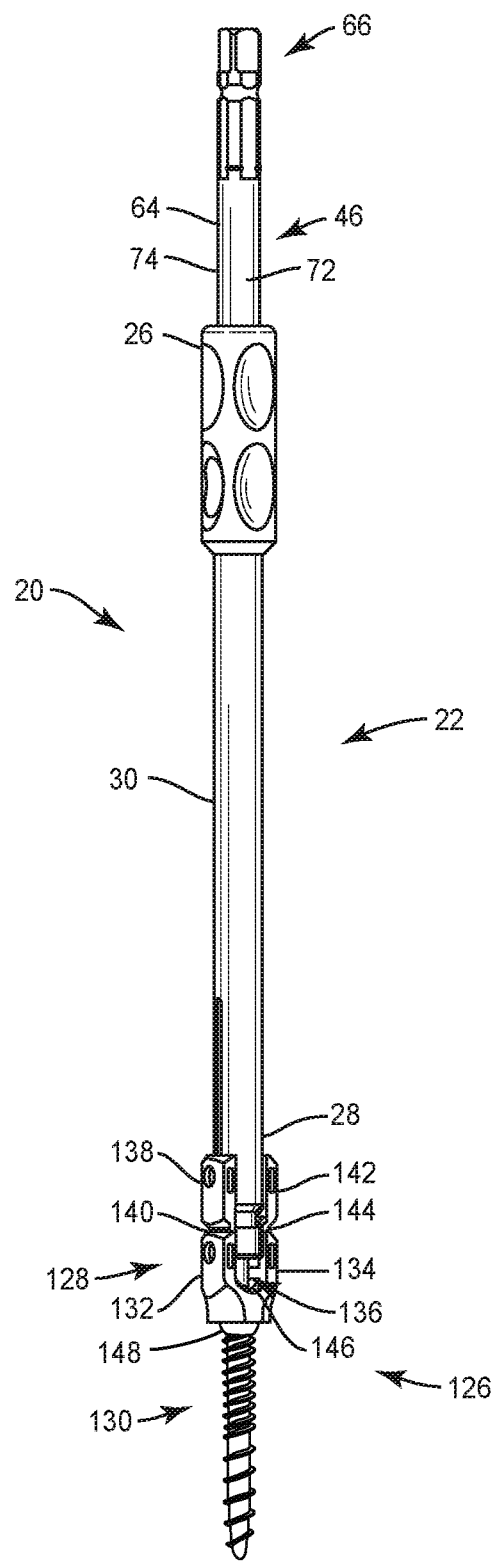
FIG. 12 is a side view of one embodiment of components of the surgical system shown in FIG. 1, in accordance with the principles of the present disclosure Like reference numerals indicate similar parts throughout the figures.

In one embodiment, shown in FIG. 12, surgical system 20 includes a bone fastener 126 that is similar to fastener 80 and fastener 116. In some embodiments, fastener 126 is the same or similar to one of the fasteners disclosed in U.S. patent application Ser. No. 15/658,635, filed on Jul. 25, 2017, which is expressly incorporated by reference herein, in its entirety. Fastener 126 is a RMAS configured for engagement with tissue and includes a receiver 128 and a screw 130. Receiver 128 includes a pair of spaced apart arms 132, 134 that define a passageway 136 therebetween configured for disposal of an implant, such as, for example, one or more spinal rods. Arms 132, 134 each include an arcuate outer surface extending between a pair of side surfaces. At least one of the outer surfaces and the side surfaces of arms 132, 134 have at least one recess or cavity therein configured to receive an insertion tool, compression instrument and/or instruments for inserting and tensioning bone fastener 126.

Arm 132 includes a break away tab 138 that is frangibly connected to arm 132 at a portion 140. In some embodiments, portion 140 is fabricated from a fracturing and/or frangible material such that manipulation of tab 138 relative to arm 140 can fracture and separate tab 138 from arm 132 along portion 140 at a predetermined force and/or torque limit, as described herein. In some embodiments, as force and/or torque is applied to tab 138 and resistance increases, for example, the predetermined torque and force limit is approached. Arm 134 includes a break away tab 142 that is frangibly connected to arm 134 at a portion 144. In some embodiments, portion 144 is fabricated from a fracturing and/or frangible material such that manipulation of tab 142 relative to arm 134 can fracture and separate tab 142 from arm 134 along portion 144 at a predetermined force and/or torque limit, as described herein. In some embodiments, as force and/or torque is applied to tab 142 and resistance increases, for example, the predetermined torque and force limit is approached.

In some embodiments, tabs 138, 142 can fracture and separate at a predetermined force or torque limit, which may be in a range of approximately 2 Newton meters (N-m) to 8 Nm. In some embodiments, tabs 138, 142 and arms 132, 134 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 138, 142 from arms 132, 134.

Passageway 136 is substantially U-shaped. In some embodiments, all or only a portion of passageway 136 may have alternate cross section configurations, such as, for example, closed, V-shaped, W-shaped, oval, oblong triangular, square, polygonal, irregular, uniform, non-uniform, offset, staggered, and/or tapered. Receiver 128 includes thread forms configured for engagement with a coupling member, such as, for example, a setscrew to retain a spinal rod within passageway 136. In some embodiments, the inner surface of receiver 128 may be disposed with the coupling member in alternate fixation configurations, such as, for example, friction fit, pressure fit, locking protrusion/recess, locking keyway and/or adhesive. In some embodiments, all or only a portion of the inner surface of receiver 128 may have alternate surface configurations to enhance engagement with a spinal rod and/or a setscrew, such as, for example, rough, arcuate, undulating, mesh, porous, semi-porous, dimpled and/or textured. In some embodiments, receiver 128 may include alternate configurations, such as, for example, closed, open and/or side access. Fastener 126 includes a crown 146 configured to facilitate positioning of a spinal rod.

Receiver 128 defines a cavity configured for disposal of a head 148 of screw 130, as described herein. Head 148 includes a tool engaging portion, such as, for example, a socket configured to engage a surgical tool or instrument, as described herein. Screw 130 is configured to penetrate tissue, such as, for example, bone and includes an outer surface having an external thread form. In some embodiments, the external thread form may include a single thread turn or a plurality of discrete threads.

In some embodiments, receiver 128 is manually engageable with head 148 in a non-instrumented assembly, as described herein. In some embodiments, manual engagement and/or non-instrumented assembly of receiver 128 and head 148 includes coupling without use of separate and/or independent instrumentation engaged with the components to effect assembly. In some embodiments, manual engagement and/or non-instrumented assembly includes a practitioner, surgeon and/or medical staff grasping receiver 128 and screw 130 and forcibly assembling the components. In some embodiments, manual engagement and/or non-instrumented assembly includes a practitioner, surgeon and/or medical staff grasping receiver 128 and screw 130 and forcibly snap fitting the components together, as described herein. In some embodiments, manual engagement and/or non-instrumented assembly includes a practitioner, surgeon and/or medical staff grasping receiver 128 and screw 130 and forcibly pop fitting the components together and/or pop fitting receiver 128 onto screw 130, as described herein. In some embodiments, a force in a range of 2-50 N is required to manually engage receiver 128 and screw 130 and forcibly assemble the components. In some embodiments, a force in a range of 5-10 N is required to manually engage receiver 128 and screw 130 and forcibly assemble the components.

In some embodiments, receiver 128 is connectable with screw 130 to include various configurations, such as, for example, a posted screw, a pedicle screw, a bolt, a bone screw for a lateral plate, an interbody screw, a uni-axial screw (IFAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

In assembly, operation and use, access to a surgical site is obtained and a particular surgical procedure is performed. The components of surgical system 20, driver 22 and fastener 126 are employed to augment the surgical treatment. For example, a tip of screw 130 is positioned adjacent to tissue, such as, for example, bone, with receiver 128 coupled to screw 130, as discussed herein. Driver 22 is delivered to surgical site with sleeve 24 oriented relative to shaft 46 in the first position (FIGS. 2 and 3) to allow for visualization of drive bit 70. Drive bit 70 is inserted into the socket in screw 130 such that axis LA1 is parallel and/or coaxial with an axis defined by screw 130.

A motorized and/or manual actuator is engaged with drive portion 66 to connect the actuator to shaft 46. The actuator can be connected with shaft 46 either before or after drive bit 70 is inserted into the socket in screw 130, depending on a particular surgical procedure. The actuator causes shaft 46 to rotate relative to sleeve 24 such that shaft 46 rotates screw 130 to drive screw 130 into the tissue.

In some embodiments, at least the first amount of force is applied to sleeve 24 to move sleeve 24 relative to shaft 46 along axis LA1 in the direction shown by arrow A in FIG. 8 to overcome the first amount of friction. Sleeve 24 is translated relative to shaft 46 along axis LA1 in the direction shown by arrow A in FIG. 8 until spring 44 is positioned in engagement portion 76, as shown in FIGS. 4 and 5, and portion 60 of sleeve 24 is positioned in passageway 136 to orient sleeve 24 relative to shaft 46 in the second position. In some embodiments, sleeve 24 is positioned in passageway 136 in the same or similar manner as sleeve is positioned in passageway 104 and/or passageway 122, as discussed herein. For example, surfaces of lugs 50, 52 and surfaces 60, 62 can engage surfaces of receiver 128 that are the same or similar to portion 90, portion 92, portion 94, portion 98, portion 100 and portion 102 of either arm 132, arm 134, or tab 138, tab 142 to prevent rotation of receiver 128 relative to sleeve 24. Drive bit 70 remains inserted into the socket in screw 130 when sleeve 24 is in the second position such that axis LA1 is parallel and/or coaxial with the axis defined by screw 130. A motorized and/or manual actuator is engaged with drive portion 66 to connect the actuator to shaft 46 while a second motorized and/or manual actuator is engaged with grip 32 of shaft 46. The first actuator rotates shaft 46 relative to sleeve 24 such that shaft 46 rotates screw 130 to drive screw 130 into the tissue while the second actuator rotates and/or maintains the orientation of sleeve 24 and with it, receiver 124 about axis LA1.

Once screw 130 is sufficiently driven into the tissue to fix screw 130 relative to the tissue, at least the second amount of translational force is applied to shaft 46 to move shaft 46 relative to sleeve 24 along axis LA1 in the direction shown by arrow B in FIG. 8 to overcome the second amount of translational friction. Shaft 46 is translated relative to sleeve 24 along axis LA1 in the direction shown by arrow B in FIG. 8 until spring 44 is positioned in engagement portion 78, as shown in FIGS. 6 and 7, which orients sleeve 24 relative to shaft 46 in the third position. As sleeve 24 moves from the second position to the third position, drive bit 70 moves out of the socket in screw 130 and into passageway 36 such that drive bit 70 is positioned entirely within passageway 36, as shown in FIG. 7. Removal of drive bit 70 from the socket in screw 130 allows receiver 128 to pivot relative to screw 130 in one or a plurality of planes. Portion 48 remains positioned in passageway 136 to prevent rotation of receiver 128 relative to sleeve 24.

In some embodiments, portion 48 is removed from passageway 136 and drive bit 70 is removed from the socket in screw 130 to disengage driver 22 from fastener 126 without orienting shaft 46 relative to sleeve 24 in the third position. For example, if passageway 136 is properly oriented for engagement and/or disposal of an implant, such as, for example, one or more spinal rods, receiver 128 is not pivoted relative to screw 130 prior to disengaging driver 22 from fastener 126. In some embodiments, receiver 128 is pivoted relative to screw 130 using driver 22 such that axis LA1 extends transverse to the axis defined by screw 130 prior to removing portion 48 from passageway 136 to selectively orient passageway 136 relative to screw 130 for engagement and/or disposal of an implant, such as, for example, one or more spinal rods, using driver 22. Once passageway 136 is selectively oriented relative to screw 130, portion 48 is removed from passageway 136 to disengage driver 22 from receiver 128. Driver 22 is then removed from the surgical site. In some embodiments, an implant, such as, for example, one or more spinal rods, is/are positioned in passageway 136 and a coupling element, such as, for example, a set screw is threaded with the threads of arms 132, 134 such that the set screw directly engages the implant(s) disposed in passageway 136 to fix the implant(s) relative to receiver 118.

In some embodiments, a kit containing one or more components of surgical system 20 is provided. The kit may comprise components from any of the embodiments discussed herein. In some embodiments, the kit comprises one or more of fasteners 80, 116, 126. In some embodiments, the kit comprises driver 22 and one or more implant, such as, for example, one or more spinal rods. In some embodiments, the kit comprises one or more coupling elements, such as, for example, one or more set screws.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A driver comprising:
 a sleeve comprising an inner surface defining a passageway, the sleeve extending along a longitudinal axis between a proximal end and an opposite distal end, the proximal end comprising a groove in the inner surface;
 a biasing element positioned partially in the groove; and
 a shaft disposed in the passageway, the shaft comprising an outer surface, a first engagement portion, and a second engagement portion,
 wherein:
  the sleeve is translatable relative to the shaft in an axial direction, along the longitudinal axis;
  the biasing element creates friction between the sleeve and the shaft, limiting relative axial motion between the sleeve and shaft, when the biasing element engages the outer surface, the first engagement portion, and the second engagement portion;
  when the biasing element engages the outer surface, a first amount of translational force is required to overcome the friction to move the sleeve relative to the shaft axially;
  when the biasing element engages the first engagement portion, a second amount of translational force, greater than the first amount of translational force, is required to overcome the friction to move the sleeve relative to the shaft axially; and
  when the biasing element engages the second engagement portion, a third amount of translational force, greater than the first amount of translational force, is required to overcome the friction to move the sleeve relative to the shaft axially.

2. A driver as recited in claim 1, wherein the outer surface includes an intermediate outer surface, between the first engagement portion and the second engagement portion, and the biasing element is caused selectively to engage the intermediate outer surface.

3. A driver as recited in claim 1, wherein the second amount of translational force is approximately equal to the third amount of translational force.

4. A driver as recited in claim 1, wherein:
 the biasing element creates friction between the sleeve and shaft, limiting relative rotational motion between the sleeve and the shaft, when the biasing element engages the outer surface, the first engagement portion, and the second engagement portion;

when the biasing element engages the outer surface, a first amount of rotational force is required to overcome the friction to move the sleeve relative to the shaft rotationally;

when the biasing element engages the first engagement portion, a second amount of rotational force, less than the first amount of rotational force, is required to overcome the friction to move the sleeve relative to the shaft rotationally; and when the biasing element engages the second engagement portion, a third amount of rotational force, less than the first amount of rotational force, is required to overcome the friction to move the sleeve relative to the shaft rotationally.

5. A driver as recited in claim 4, wherein the second amount of rotational force is approximately equal to the third amount of rotational force.

6. A driver as recited in claim 1, wherein the first amount of translational force is required to translate the sleeve relative to the shaft along the longitudinal axis when the biasing element is between the first engagement portion and the second engagement portion.

7. A driver as recited in claim 1, wherein the shaft comprises a proximal end defining a drive portion having a polygonal configuration and a distal end defining a drive bit having a hexalobe configuration, the drive bit being positioned outside of the passageway when the biasing element is engaged with the outer surface or the first engagement portion.

8. A driver as recited in claim 1, wherein the shaft comprises a proximal end defining a drive portion having a polygonal configuration and a distal end defining a drive bit having a hexalobe configuration, the drive bit being positioned entirely within the passageway when the biasing element is engaged with the second engagement portion.

9. A driver as recited in claim 1, wherein the sleeve includes a conical portion configured for disposal in a receiver of an implant, the sleeve including a lug extending from an outer surface of the conical portion, the lug being configured to prevent the receiver from pivoting relative to the sleeve.

10. A driver as recited in claim 1, wherein the first engagement portion is spaced apart from the second engagement portion.

11. A driver as recited in claim 1, wherein the first and second engagement portions are each recesses that extend into the outer surface of the adapter, the first engagement portion being spaced apart from the second engagement portion.

12. A driver as recited in claim 1, wherein the biasing element is a canted coil spring.

13. A driver as recited in claim 1, wherein the biasing element creates positive feedback when the biasing element initially engages with the first engagement portion and/or the second engagement portion.

* * * * *